United States Patent [19]

Manzer

[11] Patent Number: 5,051,537

[45] Date of Patent: Sep. 24, 1991

[54] GAS-PHASE FLUORINATION

[75] Inventor: Leo E. Manzer, Wilmington, Del.

[73] Assignee: E. I. Du Pont de Nemours and Company, Wilmington, Del.

[21] Appl. No.: 519,328

[22] Filed: May 4, 1990

Related U.S. Application Data

[63] Continuation of Ser. No. 355,868, May 19, 1989, abandoned, which is a continuation of Ser. No. 156,484, Feb. 12, 1988, abandoned.

[51] Int. Cl.$^5$ .................. C07C 17/20; C07C 19/02
[52] U.S. Cl. .................................. 570/168; 570/166
[58] Field of Search .......................... 570/166, 168

[56] References Cited

U.S. PATENT DOCUMENTS

| | | | |
|---|---|---|---|
| 2,005,710 | 6/1935 | Daudt et al. | 570/168 |
| 2,744,147 | 5/1956 | Milks | 260/653 |
| 2,744,148 | 5/1956 | Ruh et al. | 260/653 |
| 3,904,701 | 9/1975 | Schultz et al. | 570/166 |
| 4,147,733 | 4/1979 | Fiske et al. | 570/166 |

FOREIGN PATENT DOCUMENTS

| | | | |
|---|---|---|---|
| 546962 | 10/1957 | Canada | 570/16 |
| 28634 | 12/1964 | Japan | 570/168 |
| 1113658 | 5/1968 | United Kingdom | 570/166 |
| 2030981 | 4/1980 | United Kingdom | 570/168 |

*Primary Examiner*—J. E. Evans
*Attorney, Agent, or Firm*—James E. Shipley

[57] ABSTRACT

An improved process is disclosed for the manufacture of 1,1,1,2-tetrafluoroethane, more particularly, a gas-phase reaction of 1,1,1-trifluorochloroethane with hydrogen fluoride in the presence of a catalyst, a selected metal on aluminum fluoride, and molecular oxygen which process minimizes the oxidation of liberated hydrogen chloride to chlorine and water, extends catalyst life and improves yield.

12 Claims, No Drawings

GAS-PHASE FLUORINATION

This application is a continuation of Ser. No. 07/355,868 filed May 19, 1989 which in turn is a continuation of Ser. No. 07/156,484 filed Feb. 12, 1988, both now abandoned.

FIELD OF THE INVENTION

An improved process for the manufacture of 1,1,1,2-tetrafluoroethane, more particularly, a gas-phase reaction of 1,1,1-trifluorochloroethane with hydrogen fluoride in the presence of a catalyst of a selected metal on aluminum fluoride and molecular oxygen said catalyst minimizing the oxidation of liberated hydrogen chloride to chlorine and water.

BACKGROUND OF THE INVENTION

GB 2,030,981 discloses and claims a process for preparing 1,1,1,2-tetrafluoroethane which comprises reacting 1,1,1-trifluorochloroethane with hydrogen fluoride in molar excess at a temperature not lower than 300° C. in the presence of an inorganic chromium (III) compound with the introduction of from 0.002 to 0.05 mole of oxygen per mole of 1,1,1-trifluorochloroethane into the reaction system. The patent also states that a high conversion of 1,1,1-trifluorochloroethane to 1,1,1,2-tetrafluoroethane is achieved by reacting 1,1,1-trifluorochloroethane with a large excess of hydrogen fluoride at a relatively high temperature in the presence of an inorganic chromium (III) compound. In this process, deterioration of the catalyst is prevented by adding 0.002 to 0.05 mole of oxygen per mole of 1,1,1-trifluorochloroethane. When the oxygen content is below the lower limit, unsatisfactory catalyst deterioration occurs. When the oxygen content is more than the upper limit, catalyst deterioration is not a problem but the selective conversion to 1,1,1,2-tetrafluoroethane decreases. It is believed that this decrease in selectivity occurs because the catalyst promotes the oxidation of hydrogen chloride to molecular chlorine and water. [See Chemical Week, Page 18, June 24, 1987 for the use of chromium based catalysts for the oxidation of hydrochloric acid to chlorine and water.] Chlorine in the presence of HF reacts with the $CF_3CH_2Cl$ to produce $CF_3CHClF$ which in turn can react with starting material or product. This reaction with chlorine results in a significant yield loss of the desired product $CF_3CH_2F$. In addition, the formed water in combination with HF is very corrosive.

U.S. Pat. No. 2,744,148 discloses an alumina catalyst which may be promoted with a metal (chromium, cobalt, nickel, copper and palladium) and a process for fluorinating haloalkanes to highly fluorinated products. A process is disclosed which activates the catalyst and converts at least part of the alumina to basic aluminum fluorides.

U.S. Pat. No. 2,744,147 discloses a alumina catalyst which may be promoted with a metal (cobalt, nickel and chromium) and a process using the catalyst in a fluidized bed for fluorinating haloalkanes using the catalyst at a temperature between 180° to 425° C.

It is an object of this invention to provide a catalyst which will retain activity over a prolonged period of time in the presence of oxygen including high concentrations of oxygen [>0.05 mole per mole of 1,1,1-trifluorochloroethane] while minimizing the oxidation of hydrogen chloride to chlorine and water.

SUMMARY OF THE INVENTION

What has been discovered is a process for the preparation of 1,1,1,2-tetrafluoroethane by fluorination of 1,1,1-trifluorochloroethane, which process comprises
contacting in the gaseous phase at about 300° C. to about 500° C. said 1,1,1-trifluorochloroethane with HF and a catalyst comprising at least one metal, said metal selected from the group consisting of cobalt, manganese, nickel, palladium, silver and/or ruthenium on aluminum fluoride, said metal having an oxidation state greater than zero,
said contacting occurring in the presence of oxygen,
said contacting minimizing the oxidation of liberated hydrogen chloride to chlorine and water and producing a product stream containing 1,1,1,2-tetrafluoroethane and, thereafter,
separating the 1,1,1,2-tetrafluoroethane from the product stream.

DETAILS OF THE INVENTION

The invention catalyst can be prepared in any manner known to the art. For example, the invention catalyst can be prepared by impregnating alumina or aluminum oxyfluoride with a solution of at least one cobalt, manganese, nickel, palladium, silver and/or ruthenium compound which may be in the form of any soluble compound of the metal such as the oxide, oxyhalide, halide, pseudohalide, nitrate, sulfate or organic salt such as acetate, propionate and any other compound of said metals which is convertable to a metal fluoride under the reaction conditions or catalyst pretreatment conditions described herein. The halides include fluorides, chlorides and bromides. The pseudohalides include cyanides, cyanates and thiocyanates. The preferred metal is cobalt.

The total content of metal supported on the alumina expressed as the metal should be a catalytically effective amount and generally is not more than 50% by weight of the supported catalyst and preferably not more than 20% by weight of the catalyst, and usually at least 0.02% by weight of the catalyst. A more preferred range is 0.1 to 10% by weight of the catalyst.

The form of the catalyst is not critical and may be used in the form of pellets, powders or granules.

The reaction of the 1,1,1-trifluorochloroethane with HF in the presence of the catalyst of the instant invention is conducted at about 300° C. to 500° C., preferably about 350° C. to 475° C. and most preferably about 400° C. to 450° C. The contact time can vary widely depending on the degree of conversion desired and generally will be about 0.1 to 60 seconds, preferably about 10 to 30 seconds.

The amount of oxygen present during the contacting step relative to a mole of 1,1,1-trifluorochloroethane can vary but generally will range from 0.001 to 1.0 moles. The oxygen may be fed to the reactor as such or may be diluted with an inert gas such as nitrogen, helium or argon. The source of oxygen may also be air containing molecular oxygen.

The catalyst of this invention in the presence of oxygen has the ability to remain active for prolonged periods of time. For example, the use of 2% $Co/Al_2O_3$ in the absence of molecular oxygen at 450° C. with a contact time of 30 seconds resulted in a 3% decrease in the conversion of 1,1,1-trifluorochloroethane over a period of 19 hours. However, a repeat of the same experiment in the presence of 0.2 moles of molecular oxygen maintained an essentially constant conversion of 1,1,1-trifluorochloroethane over a period of 18 hours without any significant reduction in selectivity to 1,1,1,2-tetrafluoroethane.

The catalyst of the present invention in the presence of oxygen also has the ability to minimize the oxidation of hydrogen chloride to molecular chlorine and water. The main disadvantage of this side reaction is that chlorine in the presence of HF reacts with $CF_3CH_2Cl$ or product to produce $CF_3CHClF$ which in turn can react with HF to produce $CF_3CHF_2$. This reaction with chlorine results in a significant yield loss of the desired product $CF_3CH_2F$. In addition the formed water in combination with HF is very corrosive.

By minimizing the oxidation of hydrogen chloride to molecular chlorine and water is meant that the amount of chlorine produced will be of such a molar amount as to produce a combined molar yield of $CF_3CHClF$ and $CF_3CHF_2$ less than 7%.

A comparison of the results obtained using $Cr_2O_3/O_2$ vs. $CoCl_2/Al_2O_3/O_2$ shows that the latter catalyst minimizes the oxidation of hydrogen chloride to molecular chlorine as evidenced by the absence of increased production of $CF_3CHClF$ and $CF_3CHF_2$ in the product stream when compared to the same experiment in the absence of oxygen. The results are listed in the following Table.

TABLE

| | PRODUCT STREAM ANALYSIS | | | |
| | $Cr_2O_3$ | | $CoCl_2/Al_2O_3$ (2% Co) | |
| | A | B | A | B |
|---|---|---|---|---|
| $CF_3CH_2Cl$ | 48% | 49% | 53% | 54% |
| $CF_3CH_2F$ | 44% | 36% | 40% | 39% |
| $CF_3CHClF$ | 1% | 3% | 1% | 1% |
| $CF_3CHF_2$ | 1% | 8% | 1% | 1% |
| Other | 6% | 4% | 5% | 5% |

Temperature = 450° C.
A = $HF/CF_3CH_2Cl/O_2$ = 20/1/0 (moles)
B = $HF/CF_3CH_2Cl/O_2$ = 20/1/0.2 (moles)
Contact time = 10-30 seconds For $Cr_2O_3$ in the presence of $O_2$ the selectivity to $CF_3CH_2F$ is 71%; for $CoCl_2/Al_2O_3$ in the presence of $O_2$ the selectivity to $CF_3CH_2F$ is 85%.

The amount of HF should be at least a stoichiometric amount. Generally, the molar ratio of HF to 1,1,1-trifluorochloroethane can range from about 3/1 to 30/1, preferably about 3/1 to 20/1 and more preferably about 5/1 to 10/1.

During the course of the reaction, unreacted 1,1,1-trifluorochloroethane can be recycled.

The reaction of 1,1,1-trifluorochloroethane with HF may be conducted in any suitable reactor, including fixed and fluidized bed reactors. The reaction vessel should be constructed from materials which are resistant to the corrosive effects of hydrogen fluoride, such as "Hastelloy" and "Inconel".

Generally, the catalyst composition of the present invention will be pretreated with HF or other vaporizable compounds containing fluorine such as $CCl_3F$, $SiF_4$, $CCl_2F_2$, or $CHF_3$, or $CCl_2FCClF_2$ to activate the catalyst. This pretreatment is accomplished by placing the catalyst composition in a suitable container which can be the reactor to be used to perform the reaction of the instant invention, and thereafter, passing HF over the dried catalyst composition so as to partially fluorinate the catalyst. This is conveniently carried out by passing HF over the catalyst for a period of time, for example, of about 15 to 300 minutes at a temperature of, for example, about 200° C. to about 450° C. Nevertheless, this pretreatment is not essential; initial process conditions and equipment could be selected so as to activate the catalyst under initial process conditions.

Pressure is not critical. Atmospheric and superatmospheric pressures are the most convenient and are therefore preferred.

1,1,1,2-Tetrafluoroethane produced by the invention has utility as a refrigerant, blowing agent, dispersant gas for aerosol sprays, sterilant gas, etc.

EXAMPLES

In the following illustrative Examples, all parts and percentages are by weight and all temperatures are Centrigrade unless otherwise stated. All reactions used commercial HF containing only trace amounts of water. All product compositions are given in area percents.

General Procedure for Fluorination

The reactor (a 0.5 inch ID, 12 inch long "Inconel" pipe) was charged with the amount of catalyst as described in the following examples, and placed in a sand bath. The bath was gradually heated to 400° while nitrogen gas at a flow rate of 50 ml/minute was passed through the reactor to remove traces of water. The temperature was lowered and maintained at about 200° while HF and nitrogen gas (1:4 molar ratio) were passed through the reactor and the nitrogen flow was decreased with time until neat HF was being passed through the reactor. At this point, the temperature was gradually raised to 450° and maintained there for 15 to 300 minutes. X-ray difraction analysis showed the catalyst support was converted to essentially all aluminum fluoride.

While maintaining HF flow, the temperature was then adjusted to the indicated values and, thereafter, 1,1,1-trifluorochloroethane flow was started. The flows of HF, $O_2$ (air was the source of $O_2$ in all experiments), and 1,1,1-trifluorochloroethane were adjusted to give the indicated molar ratio and contact times in the Examples.

The reactor effluent was scrubbed with aqueous potassium hydroxide to remove HCl and HF and sampled on-line with a Hewlett Packard HP 5890 gas chromatograph using a 20 foot long, one-eighth inch diameter, column containing "Krytox" perfluorinated polyether on an inert support and a helium flow of 35 cc/minute. Gas chromatographic conditions were 70° for 3 minutes followed by temperature programming to 180° at a rate of 6°/minute.

EXAMPLE 1

The General Procedure for Fluorination was followed using 19.1 g (30 cc) of $CoCl_2/Al_2O_3$ (2% Co) in the form of extrudates one-twentieth inch diameter. The results of the reaction of HF with $CF_3CH_2Cl$ over the prepared catalyst are given in Table 1. For Example 1, the reaction temperature was 410°, the molar ratio of $HF/CF_3CH_2Cl/O_2$ was 10/1/0.02, and the contact time was 30 seconds.

TABLE 1

| Ex. | Time | $CF_3CH_2Cl$ | $CF_3CH_2F$ | $CF_3CHClF$ | $CF_3CHF_2$ | Other |
|---|---|---|---|---|---|---|
| 1 | 1 hr | 66.4% | 31.5% | 0.2% | 0.1% | 1.8% |

TABLE 1-continued

| Ex. | Time | $CF_3CH_2Cl$ | $CF_3CH_2F$ | $CF_3CHClF$ | $CF_3CHF_2$ | Other |
|---|---|---|---|---|---|---|
|  | 2 hr | 66.3% | 31.6% | 0.2% | 0.1% | 1.8% |
|  | 3 hr | 66.4% | 31.5% | 0.2% | 0.1% | 1.8% |
|  | 4 hr | 66.4% | 31.5% | 0.2% | 0.1% | 1.8% |
|  | 5 hr | 66.5% | 31.4% | 0.2% | 0.1% | 1.8% |
|  | 6 hr | 66.6% | 31.3% | 0.2% | 0.1% | 1.8% |
|  | 7 hr | 66.9% | 31.1% | 0.2% | 0.1% | 1.8% |
|  | 8 hr | 66.6% | 31.2% | 0.2% | 0.1% | 1.8% |
|  | 9 hr | 66.6% | 31.2% | 0.2% | 0.1% | 1.8% |

Average conversion of $CF_3CH_2Cl$ = 33.5%
Average selectivity to $CF_3CH_2F$ = 93.7%

EXAMPLE 2

The General Procedure for Fluorination was followed using 19.1 g (30 cc) of $CoCl_2/Al_2O_3$ (2% Co) in the form of extrudates one-twentieth inch diameter. The results of the reaction of HF with $CF_3CH_2Cl$ over the prepared catalyst are given in Table 2. For Example 2, the reaction temperature was 450°, the molar ratio of $HF/CF_3CH_2Cl/O_2$ was 20/1/0.2, and the contact time was 30 seconds.

TABLE 2

| Ex. | Time | $CF_3CH_2Cl$ | $CF_3CH_2F$ | $CF_3CHClF$ | $CF_3CHF_2$ | Other |
|---|---|---|---|---|---|---|
| 2 | 1 hr | 55.0% | 37.4% | 1.5% | 0.7% | 5.4% |
|  | 2 hr | 54.7% | 37.9% | 1.4% | 0.8% | 5.2% |
|  | 3 hr | 54.7% | 38.3% | 1.4% | 0.7% | 4.9% |
|  | 4 hr | 54.6% | 38.6% | 1.4% | 0.7% | 4.7% |
|  | 5 hr | 54.4% | 38.8% | 1.4% | 0.8% | 4.6% |
|  | 6 hr | 54.1% | 39.1% | 1.4% | 0.8% | 4.6% |
|  | 7 hr | 54.2% | 39.1% | 1.4% | 0.8% | 4.5% |
|  | 8 hr | 54.1% | 39.1% | 1.5% | 0.8% | 4.5% |
|  | 9 hr | 54.2% | 39.0% | 1.5% | 0.8% | 4.5% |
|  | 10 hr | 54.3% | 39.2% | 1.5% | 0.8% | 4.2% |
|  | 11 hr | 54.2% | 39.1% | 1.5% | 0.7% | 4.5% |
|  | 12 hr | 54.3% | 39.2% | 1.5% | 0.7% | 4.3% |
|  | 13 hr | 54.3% | 39.2% | 1.5% | 0.7% | 4.3% |
|  | 14 hr | 54.3% | 39.3% | 1.5% | 0.7% | 4.2% |
|  | 15 hr | 54.4% | 39.2% | 1.4% | 0.7% | 4.3% |
|  | 16 hr | 54.4% | 39.2% | 1.4% | 0.7% | 4.3% |
|  | 17 hr | 54.4% | 39.3% | 1.4% | 0.7% | 4.2% |
|  | 18 hr | 54.1% | 39.3% | 1.5% | 0.7% | 4.4% |
|  | 19 hr | 54.3% | 39.0% | 1.4% | 0.7% | 4.6% |

Average conversion of $CF_3CH_2Cl$ = 45.6%
Average selectivity to $CF_3CH_2F$ = 85.3%

EXAMPLE 3

The General Procedure for Fluorination was followed using 20.7 g (30 cc) of $MnCl_2/Al_2O_3$ (3.6% Mn) in the form of extrudates one-twentieth inch diameter. The results of the reaction of HF with $CF_3CH_2Cl$ over the prepared catalyst are given in Table 3. For Example 3, the reaction temperature was 450°, the molar ratio of $HF/CF_3CH_2Cl/O_2$ was 20/1/0.2, and the contact time was 30 seconds.

TABLE 3

| Ex. | $CF_3CH_2Cl$ | $CF_3CH_2F$ | $CF_3CHClF$ | $CF_3CHF_2$ | Other |
|---|---|---|---|---|---|
| 3 | 85.7% | 9.6% | 0% | 0% | 4.7% |

Conversion = 14.3%
Selectivity to $CF_3CH_2F$ = 67%

For Examples 4–7, the reaction was run over the prepared catalyst for a period of time which ranged between 3 and 24 hours prior to sampling the product stream.

EXAMPLES 4–5

The General Procedure for Fluorination was followed using 20.2 g (30 cc) of $RuCl_3/Al_2O_3$ (2% Ru) in the form of extrudates one-twentieth inch diameter. The results of the reaction of HF with $CF_3CH_2Cl$ over the prepared catalyst are given in Table 4. For Example 4/5, the molar ratio of $HF/CF_3CH_2Cl/O_2$ was 20/1/0.2 and the contact time was 30 seconds.

TABLE 4–5

| Ex. | Temp. | $CF_3CH_2Cl$ | $CF_3CH_2F$ | $CF_3CHClF$ | $CF_3CHF_2$ | Other |
|---|---|---|---|---|---|---|
| 4 | 350° | 70.8% | 24.6% | 1.2% | 0.5% | 2.9% |
| 5 | 450° | 50.3% | 39.4% | 0.7% | 2.4% | 7.2% |

|  | 4 | 5 |
|---|---|---|
| Conversion | 29.2% | 49.7% |
| Selectivity to $CF_3CH_2F$ | 84.2% | 78.3% |

EXAMPLE 6

The General Procedure for Fluorination was followed using 20.8 g (30 cc) of $PdCl_2/Al_2O_3$ (2% Pd) in the form of extrudates one-twentieth inch diameter. The results of the reaction of HF with $CF_3CH_2Cl$ over the prepared catalyst are given in Table 6. For Example 6, the reaction temperature was 450°, the molar ratio of HF/CF$_3$CH$_2$Cl/O$_2$ was 20/1/0.2, and the contact time was 30 seconds.

TABLE 6

| Ex. | CF$_3$CH$_2$Cl | CF$_3$CH$_2$F | CF$_3$CHClF | CF$_3$CHF$_2$ | Other |
|---|---|---|---|---|---|
| 6 | 75.0% | 13.8% | 0.0% | 0.0% | 11.2% |

Conversion = 25.0%
Selectivity to CF$_3$CH$_2$F = 55.2%

EXAMPLE 7

The General Procedure for Fluorination was followed using 20.1 g (30 cc) of AgNO$_3$/Al$_2$O$_3$ (2% Ag) in the form of extrudates one-twentieth inch diameter. The results of the reaction of HF with CF$_3$CH$_2$Cl over the prepared catalyst are given in Table 7. For Example 6, the reaction temperature was 450°, the molar ratio of HF/CF$_3$CH$_2$Cl/O$_2$ was 20/1/0.2, and the contact time was 30 seconds.

TABLE 7

| Ex. | CF$_3$CH$_2$Cl | CF$_3$CH$_2$F | CF$_3$CHClF | CF$_3$CHF$_2$ | Other |
|---|---|---|---|---|---|
| 7 | 52.1% | 41.0% | 0.0% | 0.2% | 6.7% |

Conversion = 47.9%
Selectivity to CF$_3$CH$_2$F = 85.6%

I claim:

1. A process for the preparation of 1,1,1,2-tetrafluoroethane by fluorination of 1,1,1-trifluorochloroethane, which process comprises
   contacting in the gaseous phase at about 300° C. to about 500° C. said 1,1,1-trifluorochloroethane with HF and a catalyst comprising at least one metal on aluminum fluoride,
   said HF and 1,1,1-trifluorochloroethane present at a mol ratio of about 3/1 to about 20/1,
   said metal selected from the group consisting of cobalt, manganese, nickel, palladium, silver and ruthenium,
   said contacting occurring in the presence of molecular oxygen,
   said contacting producing an amount of chlorine such that the combined molar yield of CF$_3$CHClF and CF$_3$CHF$_2$ is less than 7% and producing a product stream containing 1,1,1,2-tetrafluoroethane and, thereafter,
   separating the 1,1,1,2-tetrafluoroethane from the product stream.

2. The process of claim 1 wherein the amount of metal is about 0.02 to about 50 weight percent of the catalyst.

3. The process of claim 1 wherein the amount of metal is about 0.1 to about 10 weight percent of the catalyst.

4. The process of claim 1 wherein the HF is contacted with the 1,1,1-trifluorochloroethane at a mol ratio of about 3/1 to about 20/1, at a temperature of about 300° C. to about 500° C., and a contact time of about 0.1 to about 60 seconds.

5. The process of claim 4 wherein the HF is contacted with the 1,1,1-trifluorochloroethane at a mol ratio of about 3/1 to about 20/1, at a temperature of about 350° C. to about 475° C., and a contact time of about 10 to about 30 seconds.

6. The process of claim 1 wherein the HF is contacted with the 1,1,1-trifluorochloroethane at a mol ratio of about 5/1 to about 10/1, at a temperature of about 400° C. to about 450° C., and a contact time of about 10 to about 30 seconds.

7. The process of claim 1 wherein the metal is cobalt.

8. The process of claim 1 wherein the metal is ruthenium.

9. The process of claim 1 wherein the metal is manganese.

10. The process of claim 1 wherein the metal is nickel.

11. The process of claim 1 wherein the metal is silver.

12. The process of claim 1 wherein the metal is palladium.

* * * * *